US011492650B2

(12) United States Patent
Mandell et al.

(10) Patent No.: US 11,492,650 B2
(45) Date of Patent: Nov. 8, 2022

(54) PRODUCTION OF SELENO-BIOLOGICS IN GENOMICALLY RECODED ORGANISMS

(71) Applicants: BOARD OF REGENTS, THE UNIVERSITY OF TEXAS SYSTEM, Austin, TX (US); PRESIDENT AND FELLOWS OF HARVARD COLLEGE, Cambridge, MA (US)

(72) Inventors: Daniel J. Mandell, Brookline, MA (US); Christopher John Gregg, Melrose, MA (US); Ross Thyer, Austin, TX (US); Andrew D. Ellington, Austin, TX (US); Peter Benjamin Stranges, Somerville, MA (US)

(73) Assignees: BOARD OF REGENTS, THE UNIVERSITY OF TEXAS SYSTEM, Austin, TX (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 379 days.

(21) Appl. No.: 16/329,761

(22) PCT Filed: Aug. 30, 2017

(86) PCT No.: PCT/US2017/049354
§ 371 (c)(1),
(2) Date: Feb. 28, 2019

(87) PCT Pub. No.: WO2018/045018
PCT Pub. Date: Mar. 8, 2018

(65) Prior Publication Data
US 2019/0194713 A1 Jun. 27, 2019

Related U.S. Application Data

(60) Provisional application No. 62/537,986, filed on Jul. 28, 2017, provisional application No. 62/381,316, filed on Aug. 30, 2016.

(51) Int. Cl.
C12P 21/02 (2006.01)
C07K 14/62 (2006.01)
A61K 38/28 (2006.01)
C07K 16/00 (2006.01)
C07K 16/18 (2006.01)
C12N 15/11 (2006.01)
A61K 38/00 (2006.01)

(52) U.S. Cl.
CPC .............. *C12P 21/02* (2013.01); *A61K 38/28* (2013.01); *C07K 14/62* (2013.01); *C07K 16/00* (2013.01); *C07K 16/18* (2013.01); *C12N 15/11* (2013.01); *A61K 38/00* (2013.01); *C07K 2317/94* (2013.01)

(58) Field of Classification Search
CPC .......... C12N 9/22; C12N 15/11; C12N 15/70; C12Q 1/44; G06F 16/24; G16B 30/00; A61K 38/00; A61K 38/28; A61P 3/10; C07K 14/61; C07K 14/62; C07K 16/00; C07K 16/10; C07K 16/16; C07K 16/18; C07K 16/241; C07K 16/243; C07K 16/249; C07K 16/2863; C07K 16/32; C07K 2317/14; C07K 2317/24; C07K 2317/622; C07K 2317/94; C07K 2319/30; C12P 21/02
See application file for complete search history.

(56) References Cited

U.S. PATENT DOCUMENTS

| | | | |
|---|---|---|---|
| 9,181,318 B2 * | 11/2015 | Satoshi | C12Q 1/66 |
| 9,464,288 B2 | 10/2016 | Soll et al. | |
| 10,023,893 B2 | 7/2018 | Soll et al. | |
| 10,240,158 B2 | 3/2019 | Soll et al. | |
| 10,557,160 B2 | 2/2020 | Ellington et al. | |
| 11,155,804 B2 * | 10/2021 | Ellington | C07K 14/245 |
| 2009/0087852 A1 | 4/2009 | Gladyshev et al. | |
| 2009/0155255 A1 | 6/2009 | Glaser et al. | |
| 2010/0240038 A1 * | 9/2010 | Inouye | C07K 14/62 |
| | | | 435/6.14 |
| 2010/0298212 A1 | 11/2010 | Miao et al. | |

(Continued)

FOREIGN PATENT DOCUMENTS

| | | |
|---|---|---|
| WO | WO 01/12657 | 2/2001 |
| WO | WO 2007/075438 | 7/2007 |

(Continued)

OTHER PUBLICATIONS

Arai et al. Preparation of Selenoinsulin as a Long-Lasting Insulin Analogue. Angewandte ChemiE International Edition. vol. 56, No. 20, pp. 5522-5526. (Year: 2017).*

Aldag, Caroline, et al. "Rewiring Translation for Elongation Factor Tu-Dependent Selenocysteine Incorporation." *Angewandte Chemie International Edition* 52.5 (2013): 1441-1445.

Anderson, J. C. et al. An expanded genetic code with a functional quadruplet codon. Proc. Natl. Acad. Sci. U. S. A. 101, 7566-7571 (2004).

(Continued)

*Primary Examiner* — Marcela M Cordero Garcia
(74) *Attorney, Agent, or Firm* — Parker Highlander PLLC

(57) ABSTRACT

Polypeptides that fold into biologies are stabilized by diselenide bonds between selenocysteine amino acids. Methods to produce such polypeptides in genomically recoded organisms (GRO) can be scaled up for industrial production. Since diselenides have the same geometric bond angles and torsions as disulfides, as well as very similar bond lengths, they can be substituted into polypeptides without disrupting the three dimensional structure of the polypeptides. Diselenides render the polypeptides resistant to reduction when they are exposed to blood serum or to reducing components of blood serum or to reducing components components within cells.

10 Claims, 9 Drawing Sheets
Specification includes a Sequence Listing.

(56) References Cited

U.S. PATENT DOCUMENTS

| | | |
|---|---|---|
| 2013/0303406 A1 | 11/2013 | Kim et al. |
| 2014/0154744 A1* | 6/2014 | Soll .......... C07K 14/47 435/69.6 |
| 2014/0303084 A1 | 10/2014 | Thorn et al. |
| 2015/0050682 A1 | 2/2015 | Hondal et al. |
| 2016/0060301 A1 | 3/2016 | Jewett et al. |
| 2016/0115232 A1 | 4/2016 | Kim et al. |
| 2016/0229920 A1 | 8/2016 | Ward et al. |
| 2017/0166945 A1 | 6/2017 | Ellington et al. |
| 2018/0105854 A1 | 4/2018 | Söll et al. |
| 2019/0241640 A1* | 8/2019 | Menting .......... C07K 14/43509 |
| 2019/0316110 A1 | 10/2019 | Ellington et al. |

FOREIGN PATENT DOCUMENTS

| | | |
|---|---|---|
| WO | WO 2009/067636 | 5/2009 |
| WO | WO 2013/009868 | 1/2013 |
| WO | WO 2016/172269 | 10/2016 |
| WO | WO 2018/014091 | 1/2018 |
| WO | WO/2020/214955 | 10/2020 |

OTHER PUBLICATIONS

Arai, Kenta, et al. "Preparation of selenoinsulin as a long-lasting insulin analogue," Angewandte Chemie 129.20 (2017): 5614-5618.

Armishaw et al., Alpha-selenoconotoxins, a new class of potent alpha7 neuronal nicotinic receptor antagonists. J Biol Chem 281, 14136-43 (2006).

Chatterjee, A., Lajoie, M. J., Xiao, H., Church, G. M. & Schultz, P. G. A Bacterial Strain with a Unique Quadruplet Codon Specifying Non-native Amino Acids. Chembiochem, n/a-n/a (2014).

Chatterjee, A., Sun, S. B., Furman, J. L., Xiao, H. & Schultz, P. G. A Versatile Platform for Single- and Multiple-Unnatural Amino Acid Mutagenesis in Escherichia coli. Biochemistry 52, 1828-1837, doi:10.1021/bi4000244 (2013).

Database ENA, Accession No. ENG64632, "Escherichia coli p0305293.4 cysteine synthase A", dated Apr. 10, 2013.

Database ENA, Accession No. KJJ77964, "Escherichia coli glutamyl tRNA reductase", dated May 12, 2016.

Database UniProt, Accession No. B1ITB1, "RecName: Full= Peptide chain release factor 2", dated May 20, 2008.

Database UniProt, Accession No. F4VHX6, "RecName: Full=7-carboxy-7-deazaguanine synthase", dated Jun. 28, 2011.

Database UniProt, Accession No. G5QQB8, "RecName: Full =Aerobic respiration control sensor protein", dated Jan. 25, 2012.

Extended European Search Report and Written Opinion issued in European Application No. 17847457.3, dated Jun. 12, 2020.

Extended European Search Report and Written Opinion issued in European Application No. 17828247.1, dated Jun. 29, 2020.

Ganther et al., Selenium metabolism, selenoproteins and mechanisms of cancer prevention: complexities with thioredoxin reductase. Carcinogenesis 20, 1657-1666 (1999).

International Search Report and Written Opinion issued in International Application No. PCT/US2017/041373, dated Nov. 17, 2017.

International Search Report and Written Opinion issued in International Application No. PCT/US17/49354, dated Jan. 25, 2018.

Invitation to Pay Additional Fees issued in International Application No. PCT/US17/49354, mailed Nov. 17, 2017.

Lajoie, M. J. et al. Probing the limits of genetic recoding in essential genes.Science 342, 361-363, doi:10.1126/science.1241460 (2013).

Lajoie, Marc J., et al. "Genomically recoded organisms expand biological functions." Science 342.6156 (2013): 357-360.

Li, Xiuling, et al. "Site-specific dual antibody conjugation via engineered cysteine and selenocysteine residues." Bioconjugate Chemistry 26.11 (2015): 2243-2248.

Liu, C. C. & Schultz, P. G. Adding new chemistries to the genetic code. An. Rev. Biochem. 79, 413-444 (2010).

Liu, Hongcheng, and Kimberly May. "Disulfide bond structures of IgG molecules: structural variations, chemical modifications and possible impacts to stability and biological function." MAbs. vol. 4. No. 1. Taylor & Francis, 2012.

Mandell, Daniel J., et al. "Biocontainment of genetically modified organisms by synthetic protein design." Nature 518.7537 (2015): 55-60.

McDaniel, Timothy K., et al. "A genetic locus of enterocyte effacement conserved among diverse enterobacterial pathogens," Proceedings of the National Academy of Sciences 92.5 (1995): 1664-1668.

Miller, Corwin, et al. "A synthetic tRNA for EF-Tu mediated selenocysteine incorporation in vivo and in vitro." FEBS letters5i9A.T (2015): 2194-2199.

Moroder, Luis, et al. "Synthesis of single-and multiple-stranded cystine-rich peptides." Peptide Science: Original Research on Biomolecules 80.2-3 (2005): 85-97.

Mueller, Sabine, et al. "The formation of diselenide bridges in proteins by incorporation of selenocysteine residues: biosynthesis and characterization of (Se) 2-thioredoxin." Biochemistry 33.11 (1994): 3404-3412.

Muttenthaler et al., Modulating oxytocin activity and plasma stability by disulfide bond engineering. J Med Chem 53, 8585-96 (2010).

Neumann, H., Wang, K., Davis, L., Garcia-Alai, M. & Chin, J. W. Encoding multiple unnatural amino acids via evolution of a quadruplet-decoding ribosome. Nature 464, 441-444, (2010).

Neumann, H., Wang, K., Davis, L., Garcia-Alai, M. & Chin, J. W. Encoding multiple unnatural amino acids via evolution of a quadruplet-decoding ribosome. Nature 464, 441-444, (2010). Supplemental Information.

Ostrov, Nili, et al. "Design, synthesis, and testing toward a 57-codon genome." Science 353.6301 (2016): 819-822.

Partial European Search Report and Written Opinion issued in European Application No. 17847457.3, dated Mar. 12, 2020.

Partial European Search Report and Written Opinion issued in European Application No. 17828247.1, dated Jan. 31, 2020.

Rengby, Olle, and Elias SJ Arnér. "Titration and conditional knockdown of the prfB gene in Escherichia coli: effects on growth and overproduction of the recombinant mammalian selenoprotein thioredoxin reductase." Applied and Environmental Microbiology 73.2 (2007): 432-441.

Safavi-Hemami, Helena, et al. "Specialized insulin is used for chemical warfare by fish-hunting cone snails." Proceedings of the National Academy of Sciences 112.6 (2015): 1743-1748.

SCORE result for US 2014-0154744, SEQ ID No. 18, dated 2014. Downloaded from internet on Oct. 31, 2018, U.S. Appl. No. 15/380,560.

SCORE result for WO 2013/009868, dated 2013. Downloaded from internet on Jun. 3, 2019, U.S. Appl. No. 15/380,560.

Thyer, Ross, et al. "Evolving tRNASec for efficient canonical incorporation of selenocysteine." Journal of the American Chemical Society 137.1 (2015): 46-49.

Thyer, Ross, et al. "Custom selenoprotein production enabled by laboratory evolution of recoded bacterial strains." Nature biotechnology 36.7 (2018): 624-631.

Wang, Fei, Jana M. Carabino, and Cunegundo M. Vergara. "Insulin glargine: a systematic review of a long-acting insulin analogue." Clinical Therapeutics 25.6 (2003): 1541-1577.

Wang, L., Brock, A., Herberich, B. & Schultz, P. G. Expanding the genetic code of Escherichia coli. Science 292, 498-500 (2001).

Weil-Ktorza, Orit, et al. "Substitution of an internal disulfide bridge with a Diselenide enhances both Foldability and stability of human insulin." Chemistry—A European Journal 25.36 (2019): 8430-8430.

Young, T. S., Ahmad, I., Yin, J. A. & Schultz, P. G. An enhanced system for unnatural amino acid mutagenesis in E. coli. Journal of Molecular Biology 395, 361-374 (2009).

Betz, Stephen F. "Disulfide bonds and the stability of globular proteins." Protein Science 2.10 (1993): 1551-1558.

Dhayalan, Balamurugan, et al. "Reassessment of an innovative insulin analogue excludes protracted action yet highlights distinction between external and internal diselenide bridges." Chemistry (Weinheim an der Bergstrasse, Germany) 26.21 (2020): 4695.

Johnson, Christopher M., et al., "Thermodynamics of denaturation of mutants of barnase with disulfide crosslinks," Journal of Molecular Biology 268.1 (1997): 198-208.

(56) References Cited

OTHER PUBLICATIONS

Kjeldsen, Thomas B., et al. "Molecular Engineering of Insulin Icodec, the First Acylated Insulin Analog for Once-Weekly Administration in Humans." *Journal of Medicinal Chemistry* (2021).

Kuhlman, Brian, and Philip Bradley. "Advances in protein structure prediction and design." *Nature Reviews Molecular Cell Biology* 20.11 (2019): 681-697.

Pandyarajan, Vijay, et al. "Contribution of TyrB26 to the function and stability of insulin: structure-activity relationships at a conserved hormone-receptor interface." *Journal of Biological Chemistry* 291.25 (2016): 12978-12990.

Sciacca, L., et al. "Insulin analogues differently activate insulin receptor isoforms and post-receptor signalling." *Diabetologia* 53.8 (2010): 1743-1753.

Tidor, Brace, and Martin Karplus. "The contribution of cross-links to protein stability: A normal mode analysis of the configurational entropy of the native state." *Proteins: Structure, Function, and Bioinformatics* 15.1 (1993): 71-79.

Takei et al., "Oxidative Folding of Selenocysteine Substituted Insulin Via Interchain Diselenide Bond Formation" 52nd Japanese Peptide Symposium Lecture abstracts, 2015, vol. 52, p. 78, No. P-021.

Office Communication issued in corresponding Japanese Application No. 2019-531589, dated Jan. 7, 2022.

\* cited by examiner

| Bond | Geometry | Covalent radius (Å) | Bond length (Å) | Redox potential (mv) |
|---|---|---|---|---|
| Disulfide | | 1.02 | 2.03 | -220 |
| Diselenide | | 1.17 | 2.33 | -380 |

X-ray crystallography shows disulfides (yellow) and diselenides (red) are isosteric The redox potential of cytoplasm is -280 to -300 mV. Only diselenides can form and maintain in the cytosol Muttenthaler et al, JACS, 2010

PRODUCTION OF SELENO-BIOLOGICS IN GENOMICALLY RECODED ORGANISMS

This application is a national phase application under 35 U.S.C. § 371 of International Application No. PCT/US2017/049354, filed Aug. 30, 2017, which claims the benefit of United States Provisional Patent Application Nos. 62/381,316, filed Aug. 30, 2016, and 62/537,986, filed Jul. 28, 2017, the entirety of which are incorporated herein by reference.

This invention was made with government support under Grant no. FA9550-10-1-0169 awarded by Office of Naval Research and Grant no. N66001-14-2-4051 awarded by the Space and Naval Warfare Systems Center, Pacific. The government has certain rights in the invention.

The sequence listing that is contained in the file named "UTSBP1174US.txt", which is 3.4 MB (as measured in Microsoft Windows) and was created on Jul. 16, 2021, is filed herewith by electronic submission and is incorporated by reference herein.

TECHNICAL FIELD OF THE INVENTION

This invention is related to the area of protein biologics. In particular, it relates to methods to make protein biologics with beneficial properties.

BACKGROUND OF THE INVENTION

Protein biologics, which include monoclonal antibodies, protein therapeutics and vaccines, are effective therapies for cancer, infection, and immunological and other diseases, comprising a multi-billion dollar market. But most biologics must be made in expensive mammalian cell systems in large part because they are stabilized by chemical bonds—called disulfides—that cannot form in microbial cells. Further, because disulfide bonds are prone to chemical reduction, they can break in environments like blood serum and inside cells, so that many biologics have poor half-lives.

The vast majority of biologics—including 98% of therapeutic monoclonal antibodies—are produced in mammalian systems like Chinese hamster ovary (CHO) cells. CHO cells have the advantage of producing human-like glycosylation, and possess the necessary folding chaperones and redox machinery to produce disulfide-bearing proteins at high yield. However, CHO cells require substantially higher capital expenditures than microbial facilities, longer production times (weeks to months vs. days), many-fold higher consumables cost (e.g., media), and additional purification steps to remove endogenous retrovirus-like particles.

There are two existing approaches to producing disulfide-bearing biologics in bacteria. The first is to change the chemical environment inside the cell to become oxidizing and permissive to disulfide formation, but this change dramatically impacts central metabolism and may impair fermentation performance as well as protein production. The second approach is to secrete the nascent biologic to a smaller oxidizing compartment called the periplasm. This approach produces poor yields due to energetic losses during export, and also is highly susceptible to product loss through aggregation. Due to these shortcomings, neither approach has gained widespread adoption for large-scale production of disulfide-bearing biologics, so that more expensive mammalian bio-processes dominate. Importantly, neither approach solves the intrinsic problem that disulfide bonds are sensitive to reducing agents in environments like the cytoplasm or blood.

There is a continuing need in the art for methods of producing protein biologics in a cost effective way. There is a continuing need in the art for method of producing protein biologics that are stable in blood and cytoplasm.

SUMMARY OF THE INVENTION

According to one aspect of the invention a protein is provided which comprises at least two selenocysteine residues with at least one diselenide bond between the at least two selenocysteine residues. The protein comprises a sequence selected from the group consisting of: SEQ ID NO: 1-1632 and sequences that are at least 80% identical to said sequence. The protein may comprise a sequence selected from the group consisting of: SEQ ID NO: 1-1630 and sequences that are at least 80% identical to said sequence. The protein may comprise a sequence selected from the group consisting of: SEQ ID NO: 1631-1632 and sequences that are at least 80% identical to said sequence.

According to another aspect of the invention an antibody molecule is provided which comprises (i) a heavy chain sequence selected from the group consisting of SEQ ID NO: 472-801 and sequences that are at least 80% identical to said sequence; and (ii) a light chain sequence selected from the group consisting of SEQ ID NO: 812-1131 and sequences that are at least 80% identical to said sequence. From 0-15 pairs of selenocysteine residues in the antibody molecule are replaced with from 0-15 pairs of cysteine residues. The antibody may contain at least one diselenide bond between the heavy chain and the light chain. The antibody may contain at least one intra-chain diselenide bond within the heavy chain and/or within the light chain.

According to yet another aspect of the invention a modified insulin protein is provided. It comprises (i) an A chain having a sequence selected from SEQ ID NO: 1142, 1144, 1146, 1148, 1150, 1152, and 1154 and sequences that are at least 80% identical to said sequence; and (ii) a B chain having a sequence selected from SEQ ID NO: 1143, 1145, 1147, 1149, 1151, 1153, and 1155 and sequences that are at least 80% identical to said sequence. The protein comprises at least one diselenide bond between the A chain and the B chain.

According to one aspect of the invention a bacterial host is provided that has been genomically recoded so that an unassigned codon is recognized by a selenocysteine tRNA with a corresponding anticodon. The bacterial host contains a constructed DNA sequence encoding a variant form of a protein in which a pair of cysteine codons has been replaced with the unassigned codon. The variant form comprises a sequence selected from the group consisting of SEQ ID NO: 1-1632 and sequences that are at least 80% identical to said sequence. The variant form may comprise a sequence selected from the group consisting of SEQ ID NO: 1-1630 and sequences that are at least 80% identical to said sequence. The variant form may comprise a sequence selected from the group consisting of SEQ ID NO: 1631-1632 and sequences that are at least 80% identical to said sequence.

According to another aspect of the invention a bacterial host is provided. The bacterial host has been genomically recoded so that an unassigned codon is recognized by a selenocysteine tRNA with a corresponding anticodon. The bacterial host contains a constructed DNA sequence encoding a variant form of a monoclonal antibody in which a pair of cysteine codons has been replaced with the unassigned codon. The monoclonal antibody comprises a VL chain, and positions 23 and 88 of the VL chain are substituted with selenocysteine residues. The monoclonal antibody comprises a VH chain, and positions 22 and 92 of the VH chain are substituted with selenocysteine residues.

According to yet another aspect of the invention a method of producing a variant form of a protein is provided. The protein has a disulfide bond between cysteine residues, and the variant form has a diselenide bond between selenocysteine residues. A bacterial host that has been genomically recoded so that an unassigned codon is recognized by a selenocysteine tRNA with a corresponding anticodon is cultured. The bacterial host contains a constructed DNA sequence encoding the variant form of the protein in which a pair of cysteine codons has been replaced with the unassigned codon. The culturing is performed under conditions in which the variant form of the protein is expressed. The variant form comprises a sequence selected from the group consisting of SEQ ID NO: 1-1632 and sequences that are at least 80% identical to said sequence. The variant form may comprise a sequence selected from the group consisting of SEQ ID NO: 1-1630 and sequences that are at least 80% identical to said sequence. The variant form may comprise a sequence selected from the group consisting of SEQ ID NO: 1631-1632 and sequences that are at least 80% identical to said sequence.

According to one aspect of the invention a method of producing a variant form of a monoclonal antibody is provided. The monoclonal antibody has a disulfide bond between cysteine residues, and the variant form has a diselenide bond between selenocysteine residues. A bacterial host that has been genomically recoded so that an unassigned codon is recognized by a selenocysteine tRNA with a corresponding anticodon is cultured. The bacterial host contains a constructed DNA sequence encoding the variant form of the monoclonal antibody in which a pair of cysteine codons has been replaced with the unassigned codon. The culturing is performed under conditions in which the variant form of the monoclonal antibody is expressed. The monoclonal antibody comprises a VL chain, and positions 23 and 88 of the VL chain are substituted with selenocysteine residues. The monoclonal antibody comprises a VH chain and positions 22 and 92 of the VH chain are substituted with selenocysteine residues.

According to another aspect of the invention a method of treating a mammal with a variant form of a protein is provided. The variant form of the protein is administered to the mammal. The protein has a disulfide bond between cysteine residues. The variant form has a diselenide bond between selenocysteine residues in place of the disulfide bond between cysteine residues. The variant form comprises a sequence selected from the group consisting of SEQ ID NO: 1-1632 and sequences that are at least 80% identical to said sequence. The variant form may comprise a sequence selected from the group consisting of SEQ ID NO: 1-1630 and sequences that are at least 80% identical to said sequence. The variant form may comprise a sequence selected from the group consisting of SEQ ID NO: 1631-1632 and sequences that are at least 80% identical to said sequence.

According to yet another aspect of the invention a method is provided of treating a mammal with a variant form of a monoclonal antibody. The variant form of the monoclonal antibody is administered to the mammal. The monoclonal antibody has a disulfide bond between cysteine residues, wherein the variant form has a diselenide bond between selenocysteine residues in place of the disulfide bond between cysteine residues. The monoclonal antibody comprises a VL chain, and positions 23 and 88 of the VL chain are substituted with selenocysteine residues. The monoclonal antibody comprises a VH chain and positions 22 and 92 of the VH chain are substituted with selenocysteine residues.

According to one aspect of the invention an in vitro translation system comprising a constructed nucleic acid molecule and a tRNA molecule are provided. The constructed nucleic acid molecule encodes a variant form of a protein in which a pair of cysteine residues has been replaced with a pair of selenocysteine residues. The variant form comprises a sequence selected from the group consisting of SEQ ID NO: 1-1632 and sequences that are at least 80% identical to said sequence. The variant form may comprise a sequence selected from the group consisting of SEQ ID NO: 1-1630 and sequences that are at least 80% identical to said sequence. The variant form may comprise a sequence selected from the group consisting of SEQ ID NO: 1631-1632 and sequences that are at least 80% identical to said sequence. The nucleic acid molecule comprises an unassigned codon or leverages suppression of cognate codons to incorporate selenocysteine(s) into a growing polypeptide. The tRNA molecule is a selenocysteine tRNA with an anticodon that corresponds to the unassigned codon.

According to another aspect of the invention an in vitro translation system comprising a constructed nucleic acid molecule and a tRNA molecule is provided. The constructed nucleic acid molecule encodes a variant form of a monoclonal antibody which comprises a VL chain. Positions 23 and 88 of the VL chain are substituted with selenocysteine residues. The monoclonal antibody comprises a VH chain, and positions 22 and 92 of the VH chain are substituted with selenocysteine residues. The constructed nucleic acid molecule comprises at least a pair of cysteine codons that has been replaced with an unassigned codon in the nucleic acid. The tRNA molecule is a selenocysteine tRNA with an anticodon that is complementary to the unassigned codon.

According to yet another aspect of the invention a method is provided for producing a variant form of a protein. The protein has a disulfide bond between cysteine residues, wherein the variant form has a diselenide bond between selenocysteine residues. A constructed nucleic acid sequence encoding the variant form of the protein is translated. The constructed nucleic acid sequence comprises a pair of cysteine codons that has been replaced with an unassigned codon. The variant form comprises a sequence selected from the group consisting of SEQ ID NO: 1-1632 and sequences that are at least 80% identical to said sequence. The variant form may comprise a sequence selected from the group consisting of SEQ ID NO: 1-1630 and sequences that are at least 80% identical to said sequence. The variant form may comprise a sequence selected from the group consisting of SEQ ID NO: 1631-1632 and sequences that are at least 80% identical to said sequence. The step of translating employs a selenocysteine tRNA with a corresponding anticodon to the unassigned codon.

According to one aspect of the invention a method of testing a sample is provided. A sample is contacted with a variant form of a protein to form a reaction mixture. The protein has a disulfide bond between cysteine residues. The variant form has a diselenide bond between selenocysteine residues in place of the disulfide bond between cysteine residues. The variant form comprises a sequence selected from the group consisting of SEQ ID NO: 1-1632 and sequences that are at least 80% identical to said sequence. The variant form may comprise a sequence selected from the group consisting of SEQ ID NO: 1-1630 and sequences that are at least 80% identical to said sequence. The variant form may comprise a sequence selected from the group consisting of SEQ ID NO: 1631-1632 and sequences that are at least 80% identical to said sequence. The reaction mixture is tested to detect a specific binding partner bound to the variant form of the protein.

According to another aspect of the invention a method is provided for testing a sample. A sample is contacted with a variant form of a monoclonal antibody to form a reaction mixture. The monoclonal antibody has a disulfide bond between cysteine residues. The variant form has a diselenide bond between selenocysteine residues in place of the disulfide bond between cysteine residues. The monoclonal antibody comprises a VL chain, and positions 23 and 88 of the VL chain are substituted with selenocysteine residues. The monoclonal antibody comprises a VH chain and positions 22 and 92 of the VH chain are substituted with selenocysteine residues. The reaction mixture is tested to detect a specific binding partner bound to the variant form of the protein.

According to yet another aspect of the invention a modified antibody is provided. It comprises at least one diselenide bond.

According to one aspect of the invention a modified insulin protein is provided. It comprises an A chain having residues 90-110 of SEQ ID NO: 1630 with at least one cysteine to selenocysteine substitution; a B chain having residues 25-54 of SEQ ID NO: 1630 with at least one cysteine to selenocysteine substitution; and at least one diselenide bridge between the A chain and the B chain.

Another aspect of the invention is a modified human insulin protein comprising at least two selenocysteine residues replacing two cysteine residues in a native human insulin protein. It has at least one diselenide bond between the at least two selenocysteine residues.

These and other aspects which will be apparent to those of skill in the art upon reading the specification provide the art with methods and products for treating human and animal diseases and for making and using therapeutic, diagnostic, analytical, and prophylactic agents.

BRIEF DESCRIPTION OF THE DRAWINGS

FIG. 1 shows a comparison of properties of diselenide and disulfide bonds.

FIG. 3A-3B shows zoomed-in deconvoluted mass spectrum (FIG. 3A) and fragmentation sequence map (FIG. 3B) of 10 µM anti-MS2 scFv. Fragmentation spectra were deconvoluted using Xtract with a S/N threshold of 3 and analyzed using ProSight Lite. Formation of diselenide bonds is indicated by the lack of fragment ions between the marked selenocysteine (U) residues. No mass peaks corresponding to serine incorporation were detected. The sequence shown in FIG. 3B corresponds to SEQ ID NO: 1632.

DETAILED DESCRIPTION OF THE INVENTION

A sequence listing forms part of the disclosure of this application and is incorporated as part of the disclosure.

Figure 2:
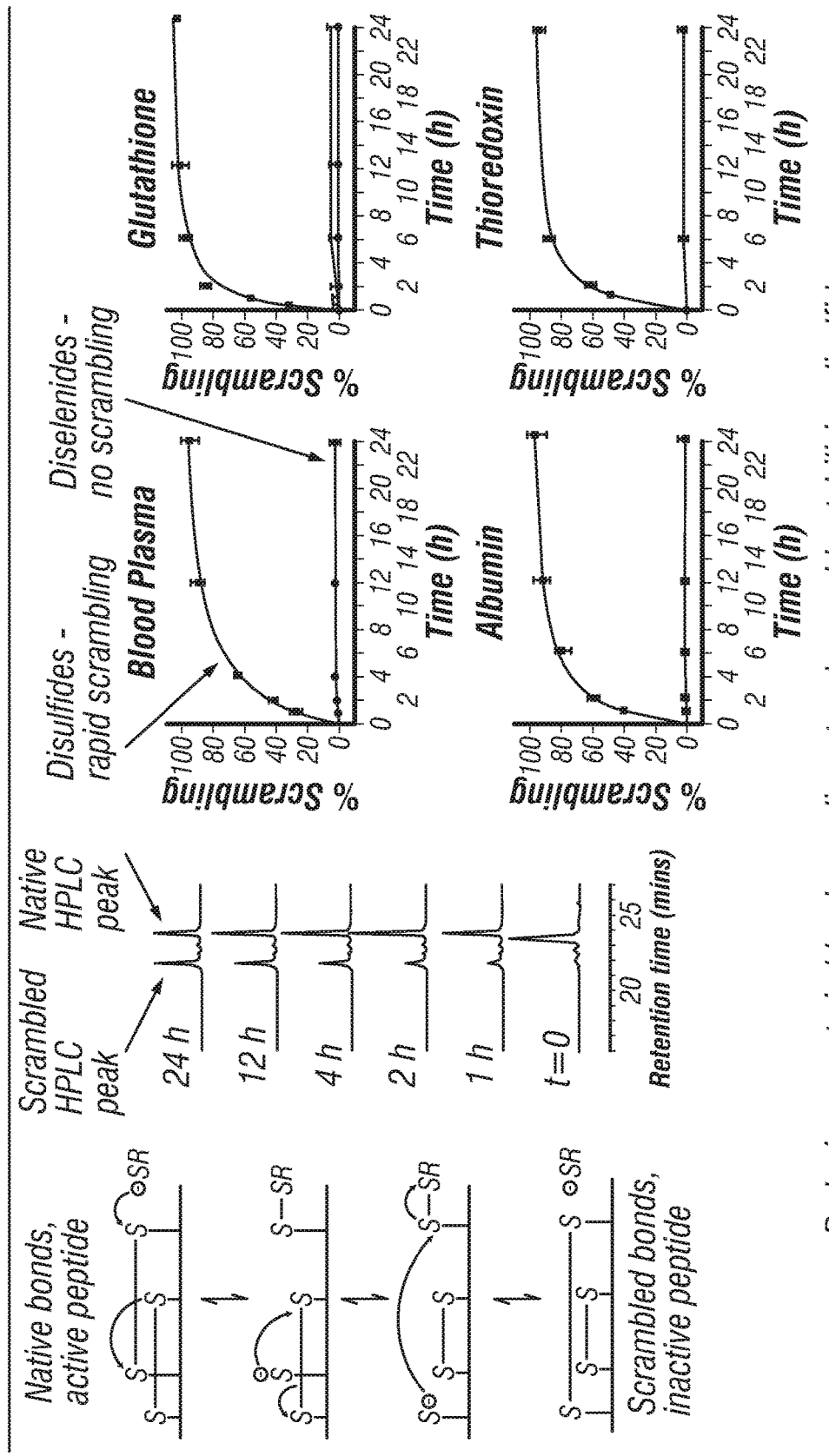
FIG. 2 shows that diselenide biologics show dramatic improvements to serum half-life over disulfides.

The inventors have developed polypeptides and methods to produce polypeptides in genomically recoded organisms (GRO) that fold into biologics that are stabilized by diselenide bonds between selenocysteine amino acids. Whereas disulfide bonds between cysteine amino acids have a redox potential of about −220 mV, diselenide bonds have a redox potential of about −380 mV. Since the bacterial cytosol typically has a redox potential of about −280 to −300 mV, diselenides but not disulfides avoid reduction so that they form and persist in the cytosol. Since diselenides have the same geometric bond angles and torsions as disulfides, as well as very similar bond lengths, they can be substituted into polypeptides without disrupting the three dimensional structure of the polypeptide (FIG. 1). Further, since intended in vivo environments like blood contain reducing agents like glutathione, albumin, and thioredoxin, disulfides in polypeptides can be reduced, causing the polypeptide to unfold and, in the case of multiple disulfides, "scramble" the disulfides so that incorrect cysteines are bonded to each other. Both of these result in abrogation of the intended biological activity of the polypeptide. The lower redox potential of diselenides renders them resistant to reduction when exposed to blood serum or purified reducing components of blood serum (FIG. 2), endowing them with a longer blood serum half-life than disulfide-bearing counterparts (Muttenhaler et al.).

While peptides bearing diselenide-forming selenocysteines may be produced in vitro by solid phase peptide synthesis (Armishaw et al., Safavi-Hemami et al.), the process does not scale tractably to the yields necessary for therapeutic applications, particularly for proteins. However, in vivo production of recombinant seleno-proteins is limited by strict sequence requirements on where selenocysteine may appear in proteins. In particular, a selenocysteine insertion sequence (SECIS) element must appear in the coding DNA sequence at the selenocysteine incorporation site in order to recruit endogenous selenocysteine translation machinery, composed of specialized enzymes (selA, selD), tRNA (selC), and an elongation factor (selB). Instead, we use a recoded strain of E. coli, which has an unassigned codon, such as an amber stop codon, together with an engineered selenocysteine tRNA with an anti-amber anticodon that permits targeted placement of selenocysteine into polypeptides by introduction of the amber stop codon into the corresponding DNA coding sequence. Typically, recoding entails removing all naturally occurring instances of the unassigned codon from the genome, as well as removing or otherwise deactivating the translational machinery associated with the unassigned codon (e.g., for amber, removing or deactivating Release Factor 1). The modified tRNA interacts with the endogenous elongation factor EF-Tu. Other codons can be recoded, typically rare codons, as is known in the art. See, Ostrov et al., Science, 353:819-822, 2016. A codon on an mRNA and an anti-codon on a tRNA are typically triplets of complementary base sequences.

Recoded proteins may be synthesized in bacteria, such as E. coli cells, or in vitro, in translation or linked transcription-translation systems. Genes or mRNA encoding such recoded proteins are non-naturally occurring, and are variants of naturally occurring coding sequences.

Although many of the proteins that we show in the associated sequence listing have all cysteine residues which participate in disulfide bonds replaced with selenocysteine residues, all cysteine residues need not be replaced to gain the benefits of the substitution. Even one diselenide bond may improve the stability of a protein. Any number of diselenide bonds (selenocysteine pairs) may be substituted for disulfide bonds in the proteins. If a protein has N disulfide bonds, the protein may have anywhere from N, N minus 1, N minus 2, N minus 3, N minus 4, . . . down to 1 such bond. Proteins with different combinations of diselenide bonds and disulfides are shown in SEQ ID NO: 1220 to 1632. It is also possible to form a bond between cysteine and selenocysteine residues called a selenylsulfide. This bond has a lower redox potential (~270 my) than a disulfide (−220 my) but not than bacterial cytoplasm (−280 my). The selenylsulfide bond may be used to increase resistance to reduction in certain redox environments. Selenylsulfides may be used in place of diselenides using methods described here by substituting selenocysteine for a single disulfide bonded cysteine, or by substituting cysteine for a single diselenide bonded selenocysteine.

Figure 3A:
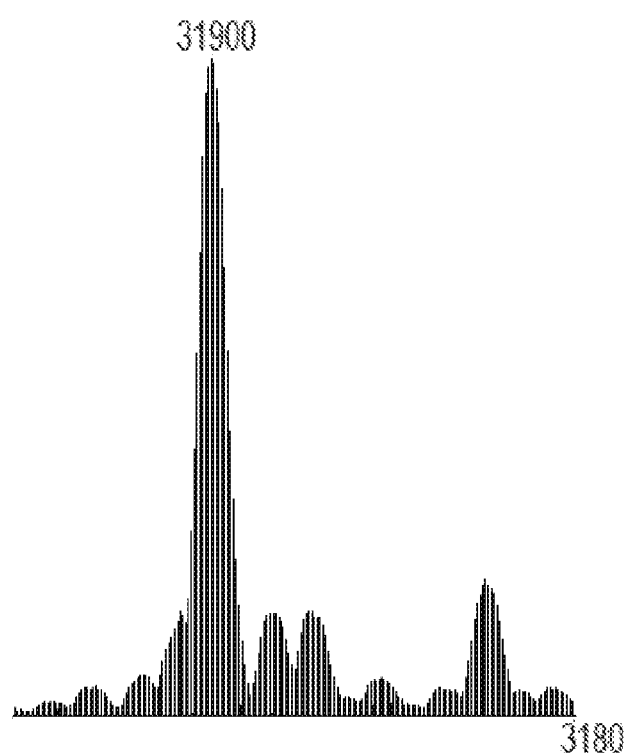

Sequences of disulfide-stabilized biologics with substituted selenocysteines can be produced in the cytosol of E. coli using our method at the mg/L scale in standard laboratory shaker flasks, and scaled to g/L production in microbial fermenters. These sequences include therapeutic proteins, vaccines, and monoclonal antibodies, antibody fragments, antibody conjugates, and other immunoglobulin-like molecules. The Fv domains may be combined with any human Fc domains. Further, any Fv domain may be produced in our system by substituting selenocysteine for cysteine at positions 23 and 88 using Kabat numbering in the variable light chain and/or by substituting selenocysteine for cysteine at positions 22 and 92 using Kabat numbering in the variable heavy chain Immunoglobulin classes IgG, IgA, IgM, IgD and IgE (including IgA1, IgA2, IgG1, IgG2, IgG3, and IgG4 subclasses) may be produced by these methods as typified classes, with any constant variant therein combined with either the Ig kappa or lambda constant light chain variants known to those in the art. Any selenocysteine in the disclosed sequences may be maintained as a cysteine so long as the presence of the cysteine does not interfere with the expression, folding, or intended function of the polypeptide. We disclose methods below for producing and verifying the presence of selenocysteines participating in the intended diselenide bonds for antibody single chain variable fragments (scFv, FIGS. 3, 6), human growth hormone (hGH, FIG. 6), PD-L1 (FIG. 4), variants of human Fc (FIG. 4), and fusions of PD-L1 and hGH to variants of human Fc (FIGS. 4 and 5), but these methods also apply to full monoclonal antibodies, other antibody fragments, antibody conjugates, other therapeutic proteins, and vaccines.

Therapeutic, diagnostic, biosensing, and prophylactic biologics may be made and used according to the invention with diselenide bonds between two selenocysteine residues. This technique and modification may be useful for any protein biologic, including but not limited to hormones (e.g., human growth hormone, FIG. 8), antibodies and antibody fragments (FIGS. 7 and 8), cytokines, growth factors, structural proteins, and the like. Insulin products, such as Lantus™, Novorapid™ Humalog™, Humulin™, Levemir™, Apidra™, and Tresiba™ may be useful with such modifications, as shown in SEQ ID NO: 1142-1155. The A chains of these insulin products can be modified as shown in SEQ ID NO: 1142, 1144, 1146, 1148, 1150, 1152, and 1154. The B chains of these insulin products can be modified as shown in SEQ ID NO: 1143, 1145, 1147, 1149, 1151, 1153, and 1155. The diselenide bonds may be intramolecular or intermolecular. Additional proteins that are suitable for such modifications include Programmed death-ligand 1 (PD-L1), PD-L1 fusion protein to an antibody domain(s), portions of PD-L1, such as the binding domain whether fused or unfused to an antibody domain(s), antibody domain(s), human growth hormone whether fused or unfused to an antibody domain(s), and Herceptin (FIGS. 4-8). This is not intended to be an exhaustive list of proteins that can be so modified.

Although particular exemplary proteins are shown with a particular sequence in the sequence listing, which forms part of this disclosure, these sequences need not be used and reproduced with total fidelity. As is known in the art, slight modifications to proteins including allelic variations and polymorphisms may occur in parts of proteins that are not detrimental to their use and function. Thus useful proteins according to the present invention may have the precise sequences which are shown in the sequence listing or they may be slightly different. For example, useful proteins may be at least 99 percent, at least 98 percent, at least 97 percent, at least 96 percent, at least 95 percent, at least 94 percent, at least 93 percent, at least 92 percent, at least 91 percent, at least 90 percent, at least 89 percent, at least 88 percent, at least 87 percent, at least 86 percent, at least 85 percent, at least 84 percent, at least 83 percent, at least 82 percent, 81 percent, or at least 80 percent identical.

The proteins that can be made according to the invention are unlimited in purpose. They can be therapeutic proteins, prophylactic proteins (such as vaccines), enzymatic proteins, endocrine proteins, signaling proteins, scaffolding proteins, diagnostic proteins, analytic proteins, etc. The diselenide bonds will generally make the proteins more stable in the presence of reducing agents.

The proteins can be made in a host cell, or in vitro, in cell-free synthetic systems. Host cells may be any that can be robustly recoded. These can be bacterial cells that have well developed genetic systems, of which E. coli is exemplary. Other bacterial species can also be used. Cell-free systems for producing the proteins may be coupled transcription/translation systems or only translation systems. A notable aspect of the methods of the invention is the use of biological syntheses rather than chemical synthesis means.

Culturing of recoded cells with the constructed nucleic acid sequences may be by any means known in the art. The culturing may be batch or continuous, in shaker flasks or in fermenters or immobilized on solid surfaces, such as small particles contained in larger vessels. Typically the culture medium will be supplemented with a source of selenium, such as $Na_2SeO_3$. As is known in the art, production of the desired protein variant may be under the control of an inducer or a repressor. Any such systems that are known in the art may be selected for convenience of construction and protein production.

Administration of a therapeutic, diagnostic, or prophylactic protein to a subject in need of such treatment may be by any means known in the art and suitable for the protein. These include without limitation intravenous, intramuscular, subcutaneous, intrathecal, oral, intracoronary, and intracranial deliveries. Certain proteins are appropriate for certain types of delivery, due to stability and target. Administration of a therapeutic protein can include one or more pharmaceutically acceptable carriers, such as, for example, a liquid or solid filler, diluent, excipient, buffer, stabilizer, or encapsulating material.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1 scFv Expression and Purification

RTAA 2X310K cells transformed with plasmid pACYC-PcaU-aMS2 bearing a gene encoding an anti-alpha MS2 scFv antibody with UAG codons directing selenocysteine incorporation substituted in place of all cysteine codons were diluted 1/250 in 1 L of terrific broth supplemented with 1000 µg·mL carbenicillin, 12.5 µg mL tetracycline and 25 µM $Na_2SeO_3$ and induced with (1 mM) 3,4-dihydroxybenzoic acid during mid log phase followed by growth O/N at 37° C. Cells were harvested by centrifugation at 8000×g for 10 min and resuspended in 25 mL of wash buffer (50 mM $K_2HPO_4$, 300 mM NaCl, 20 mM imidazole and 10% glycerol at pH 8.0) with protease inhibitor cocktail (cOmplete, mini EDTA free, Roche) and lysozyme (0.5 mg·mL$^{-1}$). Following a 20 min incubation at 4° C. with gentle agitation cells were lysed by sonication (Model 500, Fisher Scientific) and clarified three times by centrifugation at 35000×g for 30 min. Lysate was filtered through a 0.2 µm membrane and protein was recovered by IMAC using Ni-NTA resin and gravity flow columns Eluate was concentrated to 3 mL and dialyzed against TBS pH 7.5 followed by purification to apparent homogeneity by size exclusion FPLC. A significant proportion of the sample precipitated during dialysis and an additional proportion of the sample was present in the less stable/soluble dimer form. Final yield of soluble aMS2 seleno-scFv monomer was 3 mg/L.

RTΔA 2X310K-T7 cells transformed with plasmid pACYC-TetO-aTNF bearing a gene encoding an anti-TNF (tumor necrosis factor) scFv antibody with UAG codons directing selenocysteine incorporation substituted in place of all cysteine codons were diluted 1/250 in 1 L of terrific broth supplemented with 1000 µg mL carbenicillin, 33 µg·mL chloramphenicol and 25 µM $Na_2SeO_3$ and induced with 200 ng·mL anhydrotetracycline during mid log phase followed by growth O/N at 30° C. Cell were harvested and purified by IMAC as previously described. To reduce precipitation, samples were dialysed in larger volumes (>6 mL). Protein samples were purified to homogeneity by either size exclusion FPLC or anion exchange chromatography (HiTrap Q HP column) Anti-RCA, anti-GM-CSF, and anti-interferon gamma seleno-scFvs were purified by the same procedure. Final yield of soluble seleno-scFv monomers ranged between 0.5-1 mg/L.

Example 2

Mass Spectrometry

Intact protein samples were analyzed using methods described previously. Selenoprotein samples were buffer exchanged into LC-MS grade water using 10 kDa molecular weight cut-off filters. Once the buffer exchange was complete the samples were diluted to 20 µM in a methanol/water/formic acid (50/49/1) solution. After dilution, protein solutions were infused into an Orbitrap Elite mass spectrometer (Thermo Fisher Scientific Instruments, Bremen, Germany) at a rate of 3 µL·min$^{-1}$ via electrospray ionization. In order to confirm the incorporation of selenocysteine, intact mass analysis was carried out at 240 k resolution and averaging 20 scans. Characterization of the protein sequences was undertaken by ultraviolet photodissociation (UVPD) using a 193 nm excimer laser (Coherent, Inc.) which was interfaced to the Orbitrap mass spectrometer as described previously. For each UVPD spectrum, two laser pulses of 2.5 mJ were used and 250 scans were averaged. MS1 spectra were deconvoluted using the Xtract deconvolution algorithm (Thermo Fisher Scientific). UVPD mass spectra were also deconvoluted using Xtract and then analyzed using ProsightPC 3.0. Proteins containing selenocysteine were searched by adding a modification of 61.9146 Da to serine residues at the four incorporation sites (including the subtraction of one hydrogen atom due to formation of diselenide bonds). Incorporation efficiencies were calculated by dividing the area of the modified protein peak by the summed areas of the unmodified protein peak and the modified protein peak. The peak area used for each protein was the sum of the integrated areas of the five most abundant peaks from each isotope cluster.

Example 3

UAG Genomically Recoded Organism Suitable for Expressing Polypeptides with Non-Standard Amino Acids A Genomically Recoded Organism (GRO) in which the UAG codon translational function is completely removed is used to unambiguously incorporate non-standard amino acids (NSAAs) at UAG. See Lajoie, M. J. et al. Genomically recoded organisms expand biological functions. Science 342, 357-360, doi:10.1126/science.1241459 (2013), incorporated by reference in its entirety. A genomically recoded organism may include one or more reassigned triplet codons to facilitate the incorporation of non-standard amino acids (NSAAa), such as selenocysteine. Triplet codons can be reassigned to incorporate non-standard amino acids, such as selenocysteine, using methods known to those of skill in then art. See Lajoie, M. J. et al. Probing the limits of genetic recoding in essential genes. Science 342, 361-363, doi: 10.1126/science.1241460 (2013), incorporated by reference in its entirety. See also Thyer, R. et al. Evolving tRNA$^{Sec}$ for Efficient Canonical Incorporation of Selenocysteine. JACS 137(1), 46-49, (2015), incorporated by reference in its entirety. See also Ostrov, et al. Design, synthesis, and testing toward a 57-codon genome, Science 353, 819-822, 2016. Alternatively, quadruplet codons can be used to incorporate non-standard amino acids, using methods known to those of skill in the art. See Anderson, J. C. et al. An expanded genetic code with a functional quadruplet codon. Proc. Natl. Acad. Sci. U.S.A 101, 7566-7571, doi:10.1073/pnas.0401517101 (2004), Neumann, H., Wang, K., Davis, L., Garcia-Alai, M. & Chin, J. W. Encoding multiple unnatural amino acids via evolution of a quadruplet-decoding ribosome. Nature 464, 441-444, (2010) and Chatterjee, A., Lajoie, M. J., Xiao, H., Church, G. M. & Schultz, P. G. A Bacterial Strain with a Unique Quadruplet Codon Specifying Non-native Amino Acids. Chembiochem, n/a-n/a, doi: 10.1002/cbic.201402104 (2014) each of which are incorporated by reference in their entireties. An orthogonal aminoacyl-tRNA synthetase (aaRS)/tRNA pair is developed that specifically and efficiently decodes the quadruplet UAGA codon based on the non-functional UAG triplet resulting in unambiguous incorporation of non-standard amino acids, such as selenocysteine, at UAGA codons producing high protein yields. Such quadruplet codons may be used in the present methods.

Over 100 NSAAs with diverse chemistries have been synthesized and co-translationally incorporated into proteins using evolved orthogonal aminoacyl-tRNA synthetase (aaRSs)/tRNA pairs. See Liu, C. C. & Schultz, P. G. Adding new chemistries to the genetic code. An. Rev. Biochem. 79, 413-444, doi:10.1146/annurev.biochem.052308.105824 (2010), incorporated by reference in its entirety. Non-standard amino acids have been designed based on tyrosine or pyrrolysine. An aaRS/tRNA may be provided on a plasmid or into the genome of the genomically recoded organism. An orthogonal aaRS/tRNA pair is used to bioorthogonally incorporate NSAAs into proteins. Vector-based over-expression systems may be used to outcompete natural codon function with its reassigned function. See Wang, L., Brock, A., Herberich, B. & Schultz, P. G. Expanding the genetic code of Escherichia coli. Science 292, 498-500 (2001), Young, T. S., Ahmad, I., Yin, J. A. & Schultz, P. G. An enhanced system for unnatural amino acid mutagenesis in E. coli. Journal of Molecular Biology 395, 361-374 (2009), and Chatterjee, A., Sun, S. B., Furman, J. L., Xiao, H. & Schultz, P. G. A Versatile Platform for Single- and Multiple-Unnatural Amino Acid Mutagenesis in Escherichia coli. Biochemistry 52, 1828-1837, doi:10.1021/bi4000244 (2013) each of which are incorporated by reference in their entireties. If one completely abolishes natural UAG translation function, far lower aaRS/tRNA function may be sufficient to achieve efficient NSAA incorporation. GRO-based NSAA incorporation can use either vector- and/or genome-based aaRS/tRNA pairs. Genome-based aaRS/tRNA pairs have been used to reduce the mis-incorporation of canonical amino acids in the absence of available NSAAs (Mandell and Lajoie et al., Nature. 2015 Feb. 5; 518(7537):55-60. doi: 10.1038/nature14121, which is incorporated by reference).

Since the UAG codon function has been completely reassigned in the genomically recoded organism, NSAAs, such as selenocysteine, can be incorporated in the genomically recoded organism without any phenotypic consequences. NSAA incorporation in the genomically recoded organism may involve supplementing the growth media with the non-standard amino acid, such as selenocysteine, and an inducer for the aaRS. Alternatively, the aaRS may be expressed constitutively. Alternatively, as in the present disclosure, the endogenous seryl-tRNA synthetase may be used to serylate selenocysteine tRNA, which tRNA is acted upon by enzymes comprising selA and selD to produce tRNA$^{sec}$ (selenocysteine charged tRNA). Media may be supplemented with a selenium source like sodium selenite to improve production of tRNA$^{sec}$. The desired protein can be overexpressed using any desired protein overexpression system (e.g., T7-RNAP, constitutive incorporation, or inducible expression based on IPTG/allolactose, anhydrotetracycline, arabinose, rhamnose, or other inducible systems). The protein cross-link (diselenide bond) may form spontaneously based on proximity and orientation during protein folding, and the protein can be handled as any other overexpressed product.

Example 4

Methods

Sequences coding for the genes of interest were cloned into a chloramphenicol resistant vector with a T7 promoter controlled by a Tet-repressor. Vectors were transformed into 2×310 k cells with an integrated T7 RNA Polymerase controlled by a tet operon. Cells were grown to an OD~0.6 and induced with aTc at 100 ng/mL at room temperature overnight. Induced cells were pelleted and resuspended in 20 mM Tris pH 7.4, 100 mM NaCl, 20 mM imidazole, and 0.01% Triton X-100 followed by lysis by sonication. The lysates were centrifuged to separate and pellet. Supernate was run over Ni-affinity beads in the same buffer as lysis.

Figure 4:
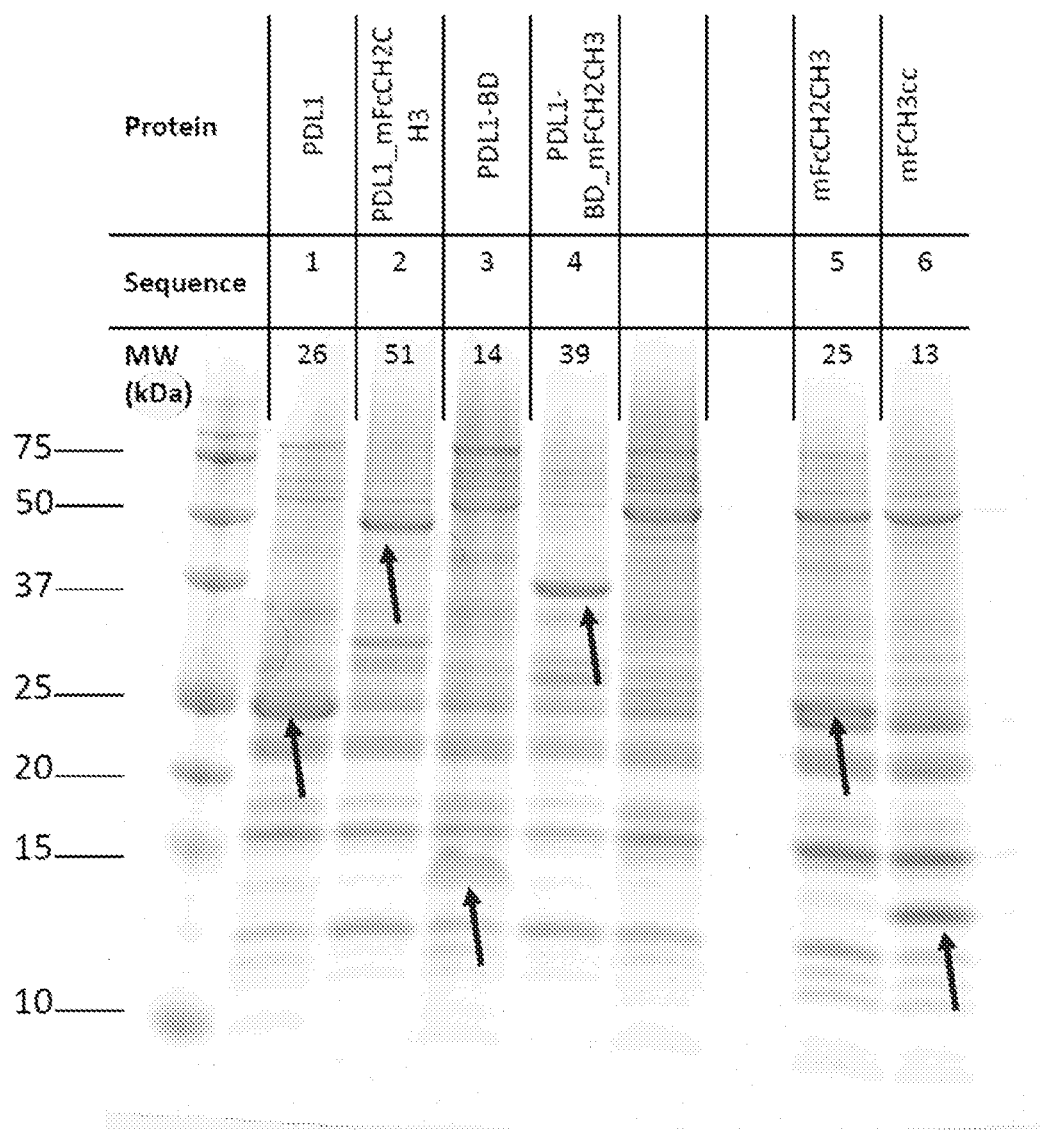
FIG. 4 shows protein expression for 6 different selenobiologics. Sequences 1-6 on the gel correspond to SEQ ID NO: 1620-1625 in the Sequence Listing. Diselenide bonds are at: SEQ ID NO: 1620 SeCys23-SeCys97 and SeCys138-SeCys192; SEQ ID NO: 1621 SeCys23-SeCys97, SeCys138-SeCys192, SeCys267-SeCys327, and SeCys373-SeCys431; SEQ ID NO: 1622 SeCys24-SeCys98; SEQ ID NO: 1623 SeCys24-SeCys98, SeCys164-SeCys224, and SeCys270-SeCys328; SEQ ID NO: 1624 SeCys32-SeCys92 and SeCys138-SeCys196; and SEQ ID NO: 1625 SeCys4-SeCys28 and SeCys86-SeCys92.
Figure 5:
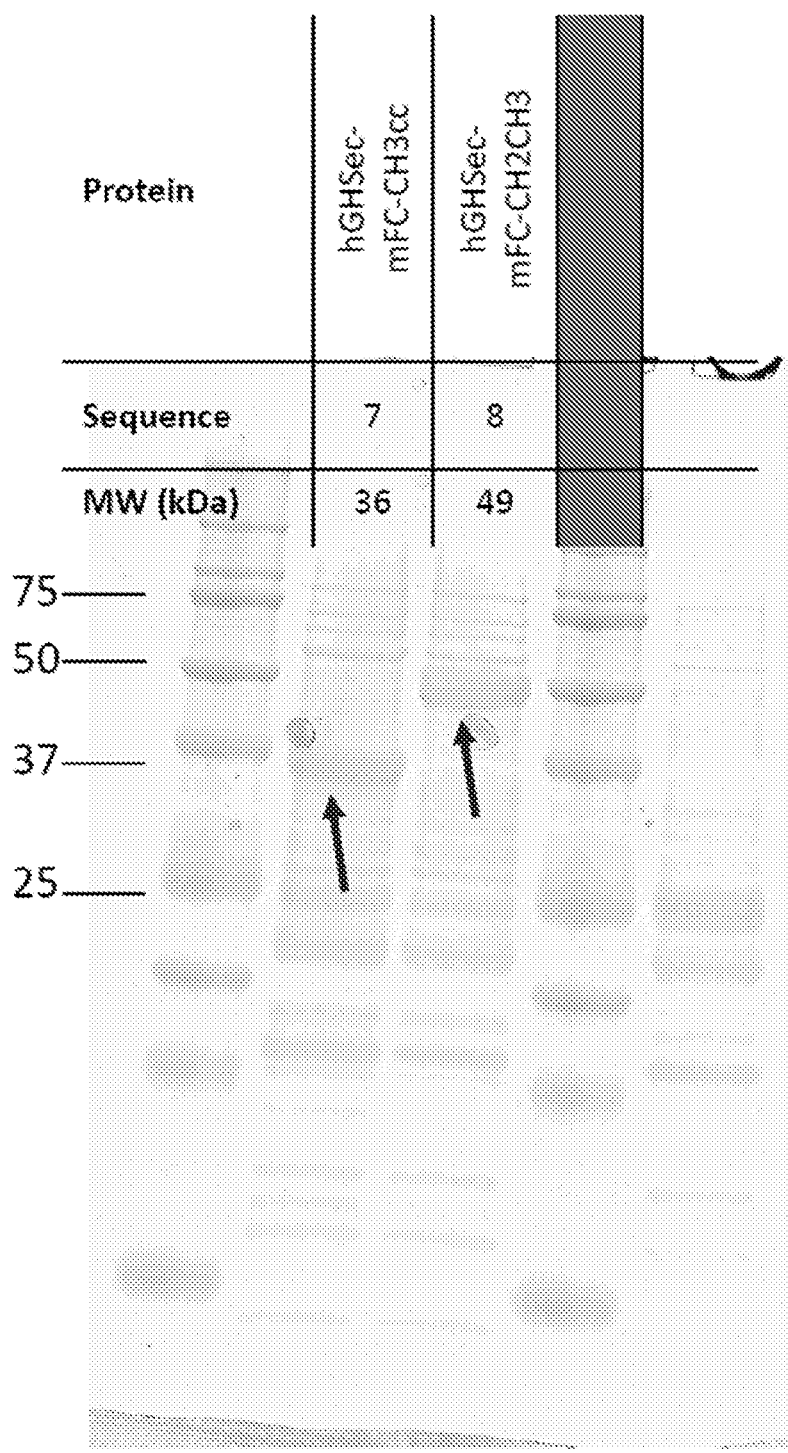
FIG. 5 shows protein expression for 2 different selenobiologics. Sequences 7-8 on the gel correspond to SEQ ID NO: 1626-1627 in the Sequence Listing. Diselenide bonds are at SEQ ID NO: 1626 SeCys183-SeCys190, SeCys210-SeCys234, and SeCys292-SeCys298; and SEQ ID NO: 1627 SeCys183-SeCys190, SeCys238-SeCys298, and SeCys344-SeCys402
Figure 6:
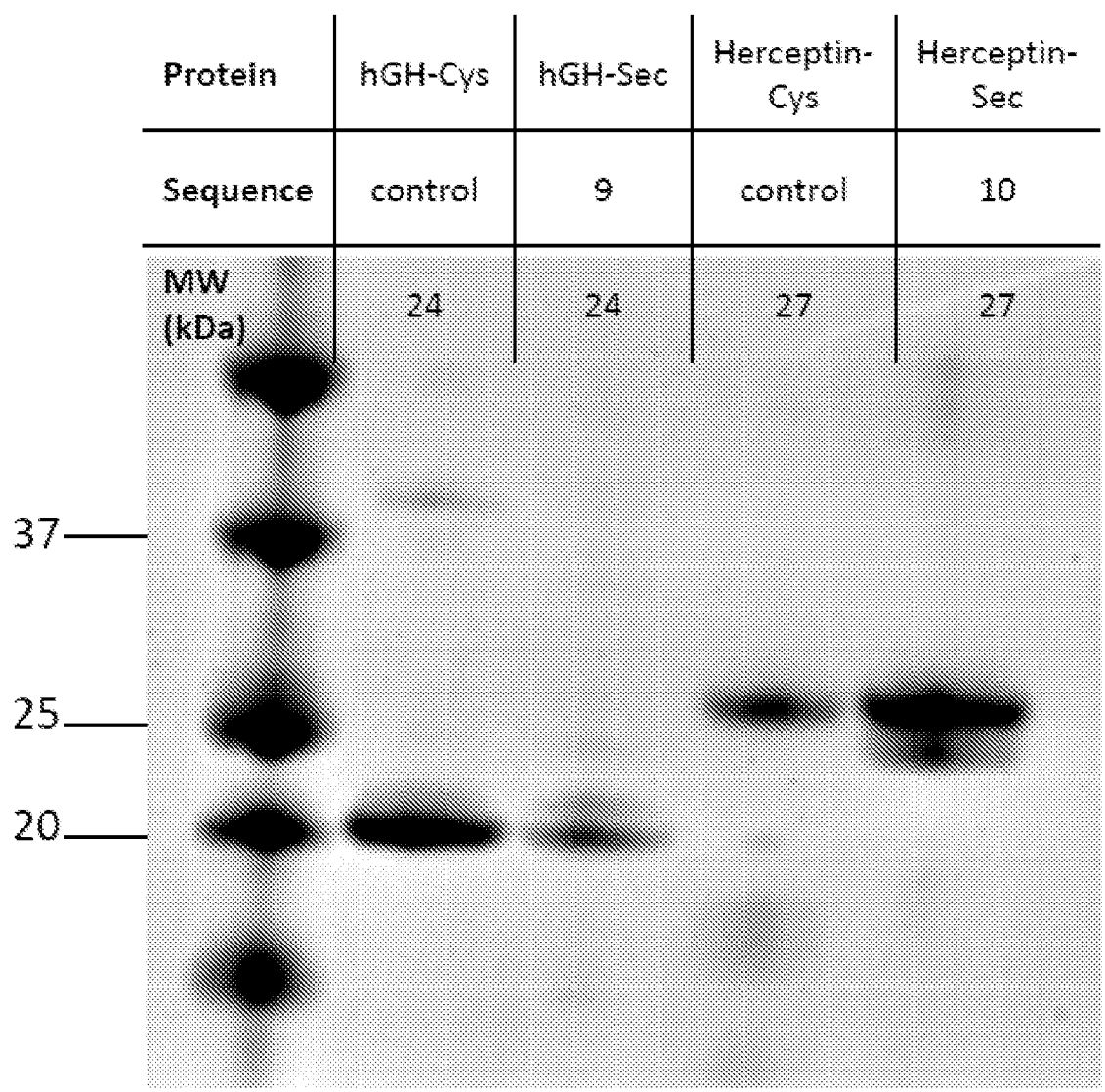
FIG. 6 shows protein expression for 2 different selenobiologics. Sequences 9-10 on the gel correspond to SEQ ID NO: 1628-1629 in the Sequence Listing. Diselenide bonds are at SEQ ID NO: 1628 SeCys54-SeCys166 and SeCys183-SeCys190; and SEQ ID NO: 1629 SeCys24-SeCys89 and SeCys149-SeCys244.
Figure 7A:
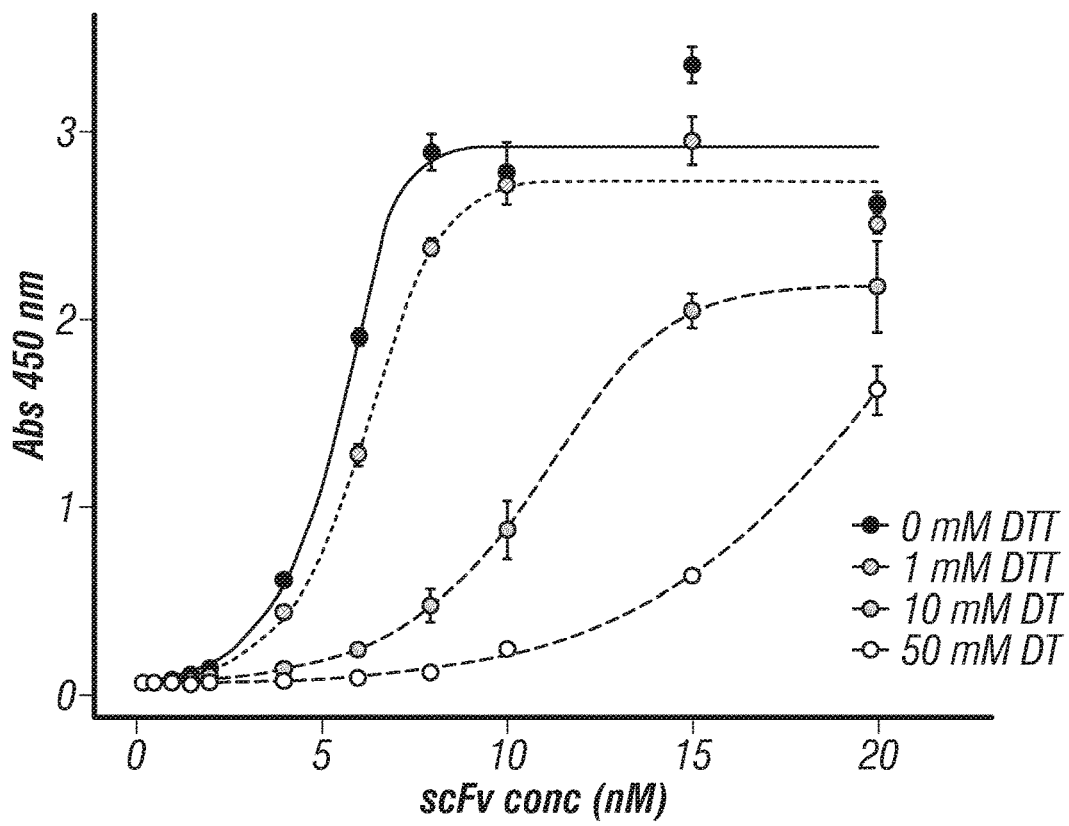
FIG. 7A-7B shows ELISA data for wild-type (disulfide) and seleno (diselenide) anti-RCA scFv in different redox conditions. Wild-type (A) and seleno (SEQ ID NO: 1631, B)-anti-RCA scFv were diluted to 1 µM in TBS pH 7.5 with 0, 1, 10 or 50 mM DTT and incubated for 16 hours at 37° C. Ricin A-chain (Sigma L9514) was diluted to 10 µg mL in PBS and bound to a 96-well plate overnight at 4° C. Control plates were bound with PBS containing 5% w/v skim milk. Plates were washed with PBS and blocked with PBS 5% w/v skim milk for two hours. Following incubation with DTT, scFvs were diluted in PBS with 5% w/v skim milk and 0.05% Tween 20 to 0, 0.25, 0.5, 1, 1.5, 2, 4, 6, 8, 10, 15 and 20 nM and bound in quadruplicate for two hours at 25° C. Secondary antibody (anti-polyhistidine-HRP, Sigma A7058) was diluted 1/10,000 in PBS with 5% w/v skim milk and 0.05% Tween 20 and bound for two hours at 25° C. Plates were incubated with TMB for 10 minutes at 25° C. with agitation and color development terminated by the addition of 2M H2SO4. Absorbance was immediately measured at 450 nm. All binding, blocking and enzymatic steps were performed on an orbital shaker at 450 rpm, and all washes were performed with PBS or PBS with 0.05% Tween 20. Only wild-type anti-RCA scFv showed substantial loss of binding at 1 and 10 mM DTT, and loss of binding was substantially abrogated at all concentrations for seleno-anti-RCA compared to WT scFv.
Figure 7B:
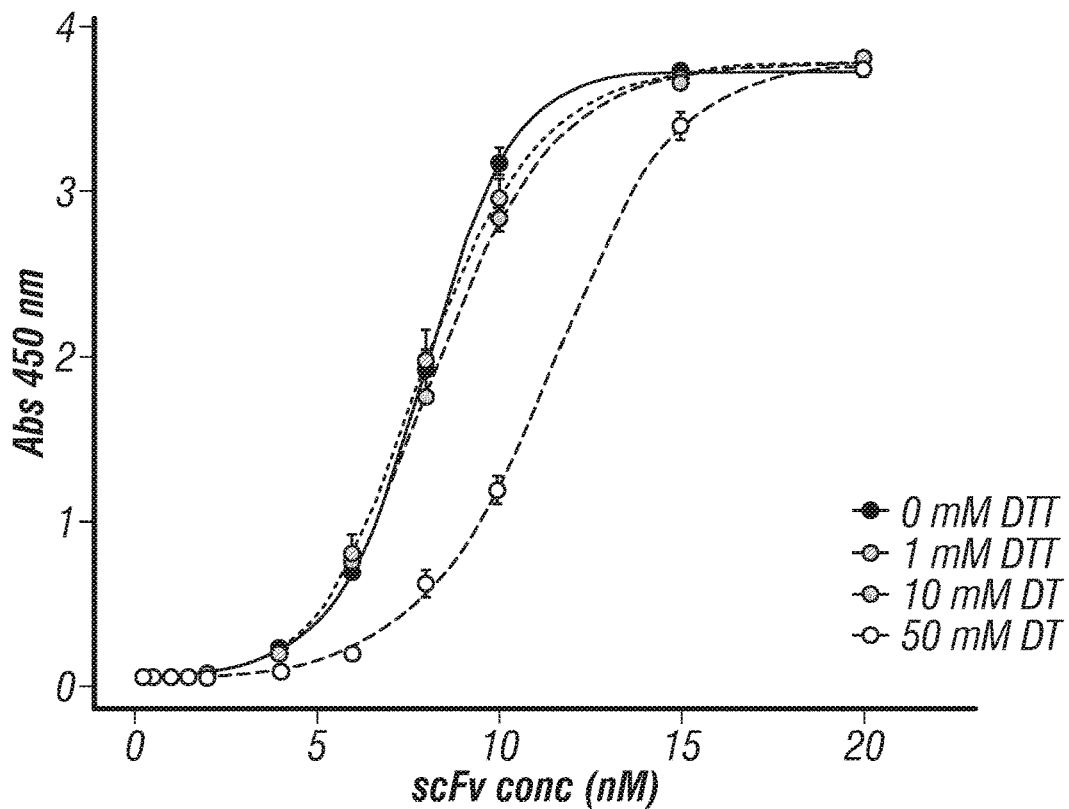
Figure 8A:
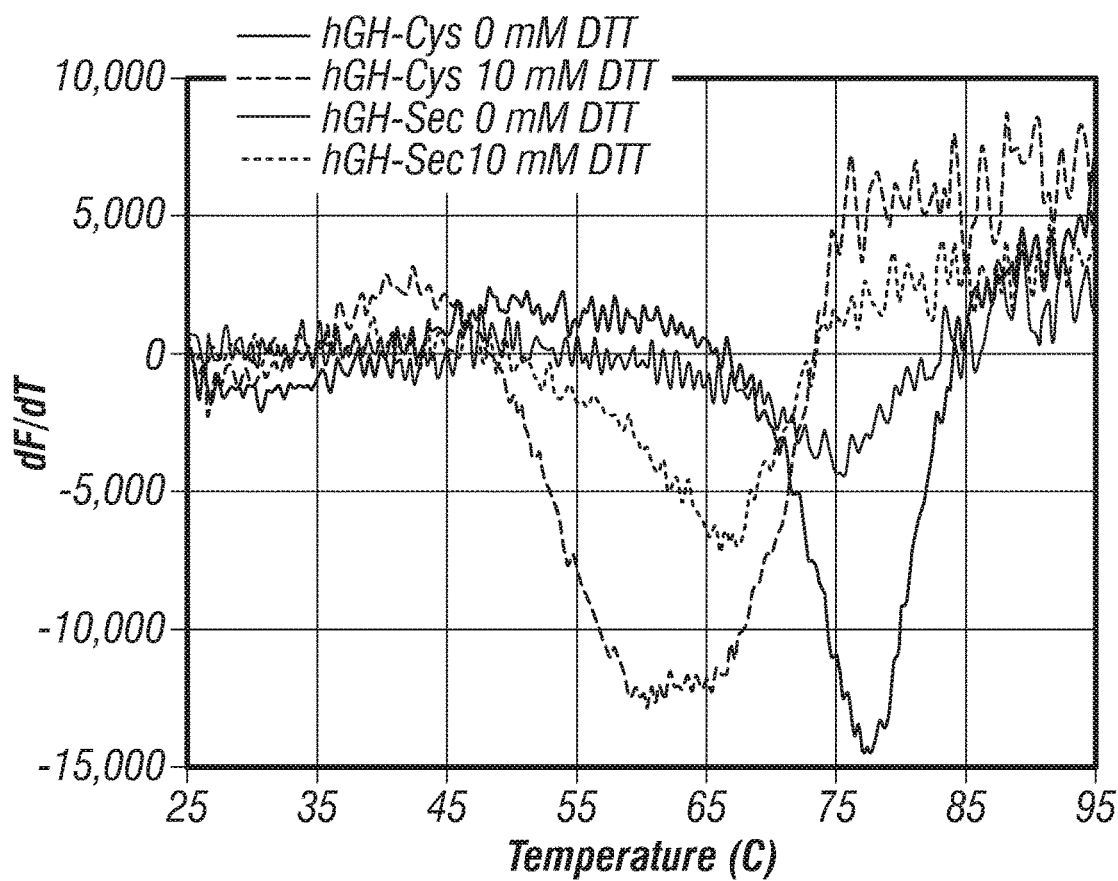
FIG. 8A-8B shows thermal shift data for wild-type (disulfide) and seleno (diselenide) variants of 2 different biologics. Thermal denaturation of purified wild-type and seleno (SEQ ID NO: 1132) hGH (A) and wild-type and seleno (SEQ ID NO: 1632) Herceptin scFv (B) in different reducing conditions was monitored using the Applied Biosystems Protein Thermal Shift dye on a QuantStudio 3 Real Time PCR system. The reducing agent DTT was added to triplicates of 5 µg of hGH-Cys/SeCys and 2 µg of Herceptin scFv-Cys/SeCys at concentrations of 0 M and 10 mM followed by incubation for 10 minutes at room temperature. The proteins were denatured in a linear ramp of 0.03° C./s from 25° C. to 98° C. Melting temperature ($T_m$) was determined by finding the minimum of dF/dT with Protein Thermal Shift Software (ThermoFisher). The hGH samples (A) showed a single minimum at both concentrations of DTT. The $T_m$ for hGH-Cys decreased from 77° C. without DTT to 60° C. in the presence of 10 mM DTT. The SeCys variant showed a marked stabilization under reducing conditions compared to the Cys variant, with a $T_m$ of 75° C. without DTT and a $T_m$ of 66° C. in 10 mM DTT. For Herceptin (B) the Cys variant showed two minima of dF/dT in both conditions. With addition of 10 mM DTT the dominant $T_m$ minima shifted from the minima at a higher temperature (70° C.) to the lower temperature (58° C.). In contrast, Herceptin-SeCys only had one minimum in both concentrations of DTT. Again, the SeCys variant showed stabilization under reducing conditions, with the $T_m$ decreasing from 68 C without DTT to 64 C in 10 mM DTT.
Figure 8B:
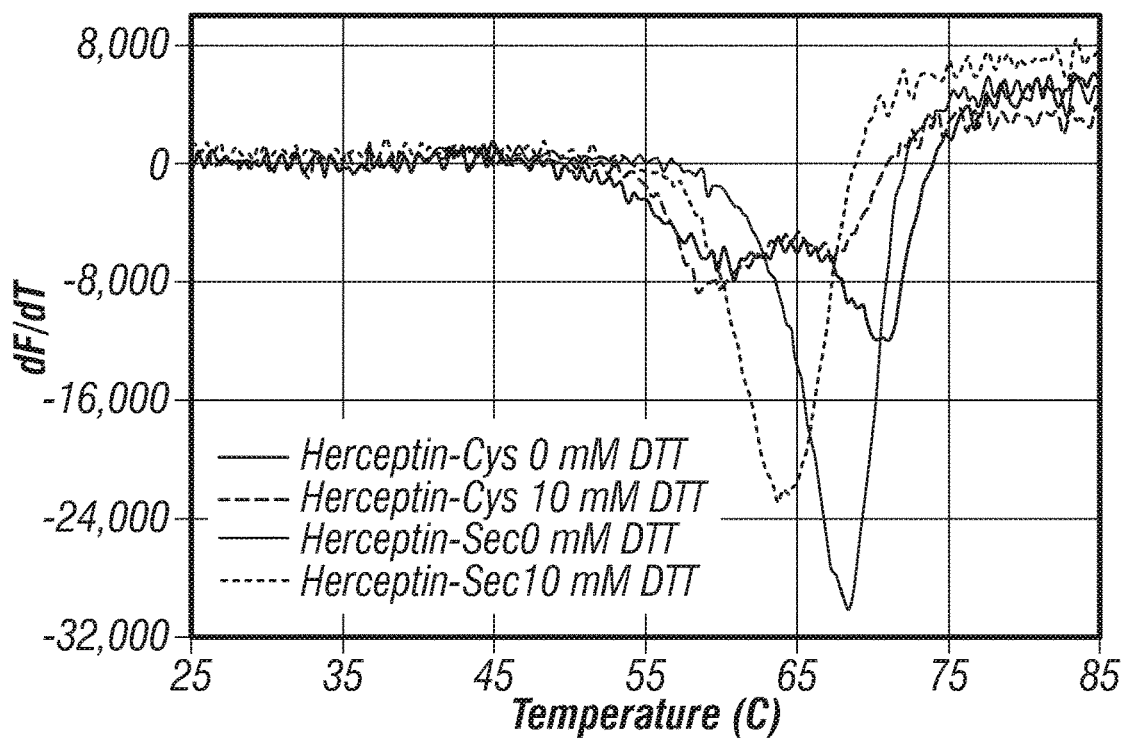

Proteins of interest were eluted in PBS pH7.4 with addition of 300 mM imidazole. Purified fractions were run on a SDS page gel. The results for 10 different selenobiologics are shown in FIGS. 4-6.

REFERENCES

The disclosure of each reference cited is expressly incorporated herein.
1. Anderson, J. C. et al. An expanded genetic code with a functional quadruplet codon. *Proc. Natl. Acad. Sci. U.S.A* 101, 7566-7571, doi:10.1073/pnas.0401517101 (2004),
2. Armishaw, C. J., Daly, N. L., Nevin, S. T., Adams, D. J., Craik, D. J. & Alewood, P. F. Alpha-selenoconotoxins, a new class of potent alpha7 neuronal nicotinic receptor antagonists. *J Biol Chem* 281, 14136-43 (2006).
3. Chatterjee, A., Lajoie, M. J., Xiao, H., Church, G. M. & Schultz, P. G. A Bacterial Strain with a Unique Quadruplet Codon Specifying Non-native Amino Acids. *Chembiochem*, n/a-n/a, doi:10.1002/cbic.201402104 (2014)
4. Chatterjee, A., Sun, S. B., Furman, J. L., Xiao, H. & Schultz, P. G. A Versatile Platform for Single- and Multiple-Unnatural Amino Acid Mutagenesis in *Escherichia coli*. Biochemistry 52, 1828-1837, doi:10.1021/bi4000244 (2013)
5. Lajoie, M. J. et al. Genomically recoded organisms expand biological functions. Science 342, 357-360, doi: 10.1126/science.1241459 (2013)
6. Lajoie, M. J. et al. Probing the limits of genetic recoding in essential genes. *Science* 342, 361-363, doi:10.1126/science.1241460 (2013)
7. Liu, C. C. & Schultz, P. G. Adding new chemistries to the genetic code. *An. Rev. Biochem.* 79, 413-444, doi: 10.1146/annurev.biochem.052308.105824 (2010)
8. Mandell and Lajoie et al., *Nature*. 2015 Feb. 5; 518(7537): 55-60. doi: 10.1038/nature14121,
9. Muttenthaler, M., Andersson, A., de Araujo, A. D., Dekan, Z., Lewis, R. J. & Alewood, P. F. Modulating oxytocin activity and plasma stability by disulfide bond engineering. *J Med Chem* 53, 8585-96 (2010).
10. Neumann, H., Wang, K., Davis, L., Garcia-Alai, M. & Chin, J. W. Encoding multiple unnatural amino acids via evolution of a quadruplet-decoding ribosome. *Nature* 464, 441-444, (2010)
11. Ostrov, et al. Design, synthesis, and testing toward a 57-codon genome, *Science* 353, 819-822, 2016
12. Safavi-Hemami, H., Gajewiak, J., Karanth, S., Robinson, S. D., Ueberheide, B., Douglass, A. D., Schlegel, A., Imperial, J. S., Watkins, M., Bandyopadhyay, P. K., Yandell, M., Li, Q., Purcell, A. W., Norton, R. S., Ellgaard, L. & Olivera, B. M. Specialized insulin is used for chemical warfare by fish-hunting cone snails. *Proc Natl Acad Sci USA* 112, 1743-8 (2015).
13. Thyer, R. et al. Evolving tRNA$^{Sec}$ for Efficient Canonical Incorporation of Selenocysteine. *JACS* 137(1), 46-49, (2015)
14. Wang, L., Brock, A., Herberich, B. & Schultz, P. G. Expanding the genetic code of *Escherichia coli*. Science 292, 498-500 (2001)
15. Young, T. S., Ahmad, I., Yin, J. A. & Schultz, P. G. An enhanced system for unnatural amino acid mutagenesis in *E. coli*. Journal of Molecular Biology 395, 361-374 (2009),

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11492650B2). An electronic copy of the "Sequence Listing" will also be available from the USPTO upon request and payment of the fee set forth in 37 CFR 1.19(b)(3).

The invention claimed is:

1. A protein comprising at least two selenocysteine residues with at least one diselenide bond between the at least two selenocysteine residues, wherein the protein comprises a sequence selected from the group consisting of: SEQ ID NO: 1142, 1144, 1146, 1148, 1150, 1152, 1154 and residues 90-110 of SEQ ID NO: 1630 and sequences that are at least 80% identical to said sequence.

2. The protein of claim 1, wherein the protein is a modified insulin protein that further comprises a B chain having a sequence of residues 25-54 of SEQ ID NO: 1630 with at least one cysteine to selenocysteine substitution and sequences that are at least 80% identical to said sequence; wherein the protein comprises at least one diselenide bond within the A chain and at least one diselenide bond between the A chain and the B chain.

3. A bacterial host that has been genomically recoded so that an unassigned codon is recognized by a selenocysteine tRNA with a corresponding anticodon, wherein the bacterial host contains a constructed DNA sequence encoding a variant form of a protein in which a pair of cysteine codons has been replaced with the unassigned codon wherein the variant form comprises a modified insulin protein having at least two selenocysteine residues replacing two cysteine residues that form a disulfide bond in a native human insulin protein, with at least one diselenide bond between the at least two selenocysteine residues.

4. A method of producing a modified insulin protein having at least two selenocysteine residues replacing two cysteine residues that form a disulfide bond in a native human insulin protein, with at least one diselenide bond between the at least two selenocysteine residues, the method comprising:
    culturing a bacterial host that has been genomically recoded so that an unassigned codon is recognized by a selenocysteine tRNA with a corresponding anticodon, wherein the bacterial host contains a constructed DNA sequence encoding the modified protein in which a pair of cysteine codons has been replaced with the unassigned codon, wherein the culturing is under conditions in which the modified protein is expressed.

5. The bacterial host of claim 3, wherein the modified insulin protein has an A chain comprising at least two selenocysteine residues with at least one diselenide bond between the at least two selenocysteine residues, wherein the protein comprises a sequence selected from the group consisting of: SEQ ID NO: 1142, 1144, 1146, 1148, 1150, 1152, 1154 and residues 90-110 of SEQ ID NO: 1630 and sequences that are at least 80% identical to said sequence.

6. The bacterial host of claim 5, wherein the modified insulin protein further comprises a B chain having a sequence of residues 25-54 of SEQ ID NO: 1630 with at least one cysteine to selenocysteine substitution and sequences that are at least 80% identical to said sequence; wherein the protein comprises at least one diselenide bond within the A chain and at least one diselenide bond between the A chain and the B chain.

7. The bacterial host of claim 3, wherein the modified insulin protein comprises an A chain having a sequence of residues 90-110 of SEQ ID NO: 1630 with at least one cysteine to selenocysteine substitution and sequences that are at least 80% identical to said sequence, and a B chain having a sequence of residues 25-54 of SEQ ID NO: 1630 with at least one cysteine to selenocysteine substitution and sequences that are at least 80% identical to said sequence; wherein the protein comprises at least one diselenide bond between the A chain and the B chain.

8. The method of claim 4, wherein the modified insulin protein has an A chain comprising at least two selenocysteine residues with at least one diselenide bond between the at least two selenocysteine residues, wherein the protein comprises a sequence selected from the group consisting of: SEQ ID NO: 1142, 1144, 1146, 1148, 1150, 1152, 1154 and residues 90-110 of SEQ ID NO: 1630 and sequences that are at least 80% identical to said sequence.

9. The method of claim 8, wherein the modified insulin protein further comprises a B chain having a sequence of residues 25-54 of SEQ ID NO: 1630 with at least one cysteine to selenocysteine substitution and sequences that are at least 80% identical to said sequence; wherein the protein comprises at least one diselenide bond within the A chain and at least one diselenide bond between the A chain and the B chain.

10. The method of claim 4, wherein the modified insulin protein comprises an A chain having a sequence of residues 90-110 of SEQ ID NO: 1630 with at least one cysteine to selenocysteine substitution and sequences that are at least 80% identical to said sequence, and a B chain having a sequence of residues 25-54 of SEQ ID NO: 1630 with at least one cysteine to selenocysteine substitution and sequences that are at least 80% identical to said sequence; wherein the protein comprises at least one diselenide bond between the A chain and the B chain.

* * * * *